United States Patent
Ramans

(10) Patent No.: US 6,206,903 B1
(45) Date of Patent: Mar. 27, 2001

(54) SURGICAL TOOL WITH MECHANICAL ADVANTAGE

(75) Inventor: Andris D. Ramans, Mountain View, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

(21) Appl. No.: 09/415,783

(22) Filed: Oct. 8, 1999

(51) Int. Cl.[7] .................................................. A61B 17/28
(52) U.S. Cl. .............................................................. 606/205
(58) Field of Search .................................. 606/205, 206, 606/207, 208, 210, 211

(56) References Cited

U.S. PATENT DOCUMENTS

| | | | |
|---|---|---|---|
| 5,275,608 | 1/1994 | Forman et al. | 606/170 |
| 5,376,094 | 12/1994 | Kline | 606/113 |
| 5,562,700 * | 10/1996 | Huitema et al. | 606/207 |
| 5,570,920 * | 11/1996 | Crisman et al. | 294/111 |
| 5,667,476 | 9/1997 | Frassica et al. | 600/149 |
| 5,817,119 | 9/1998 | Klieman et al. | 606/174 |

* cited by examiner

Primary Examiner—Michael Buiz
Assistant Examiner—Vy Q. Bui
(74) Attorney, Agent, or Firm—Townsend and Townsend and Crew LLP

(57) ABSTRACT

A robotic surgical tool includes an end effector having a pair of fingers and incorporating a mechanical advantage. In specific embodiments, a pulley and cable mechanism is used to actuate the end effector by applying cable tension. The coupling between the pulleys and the fingers of the end effector takes advantage of changes in moment arms for force transfer to avoid or minimize force reduction between the applied cable tension and the resultant force at or near the distal tip of each finger. In some embodiments, the coupling of the pulleys and fingers results in a force gain, a moment gain, or both.

26 Claims, 11 Drawing Sheets

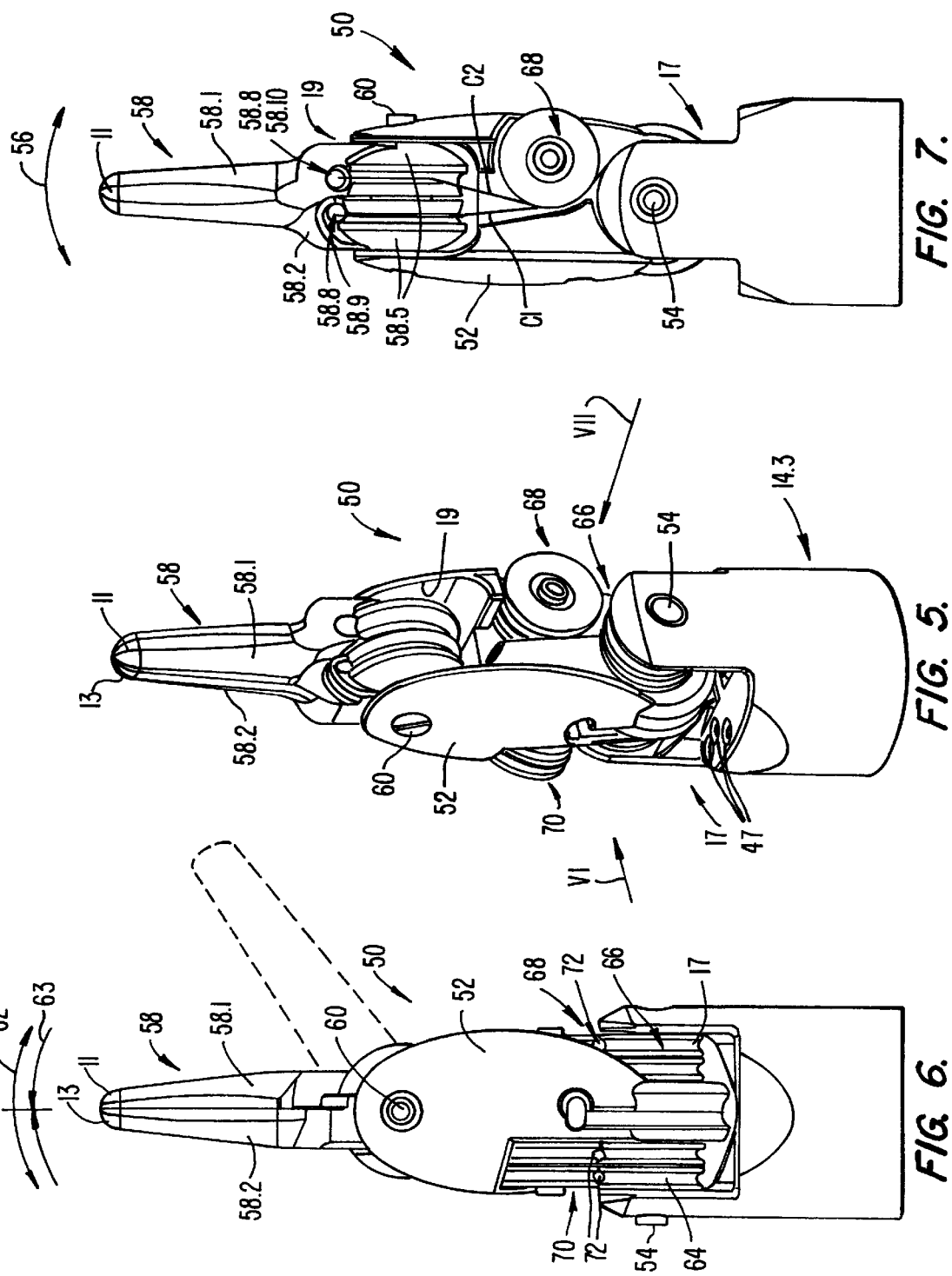

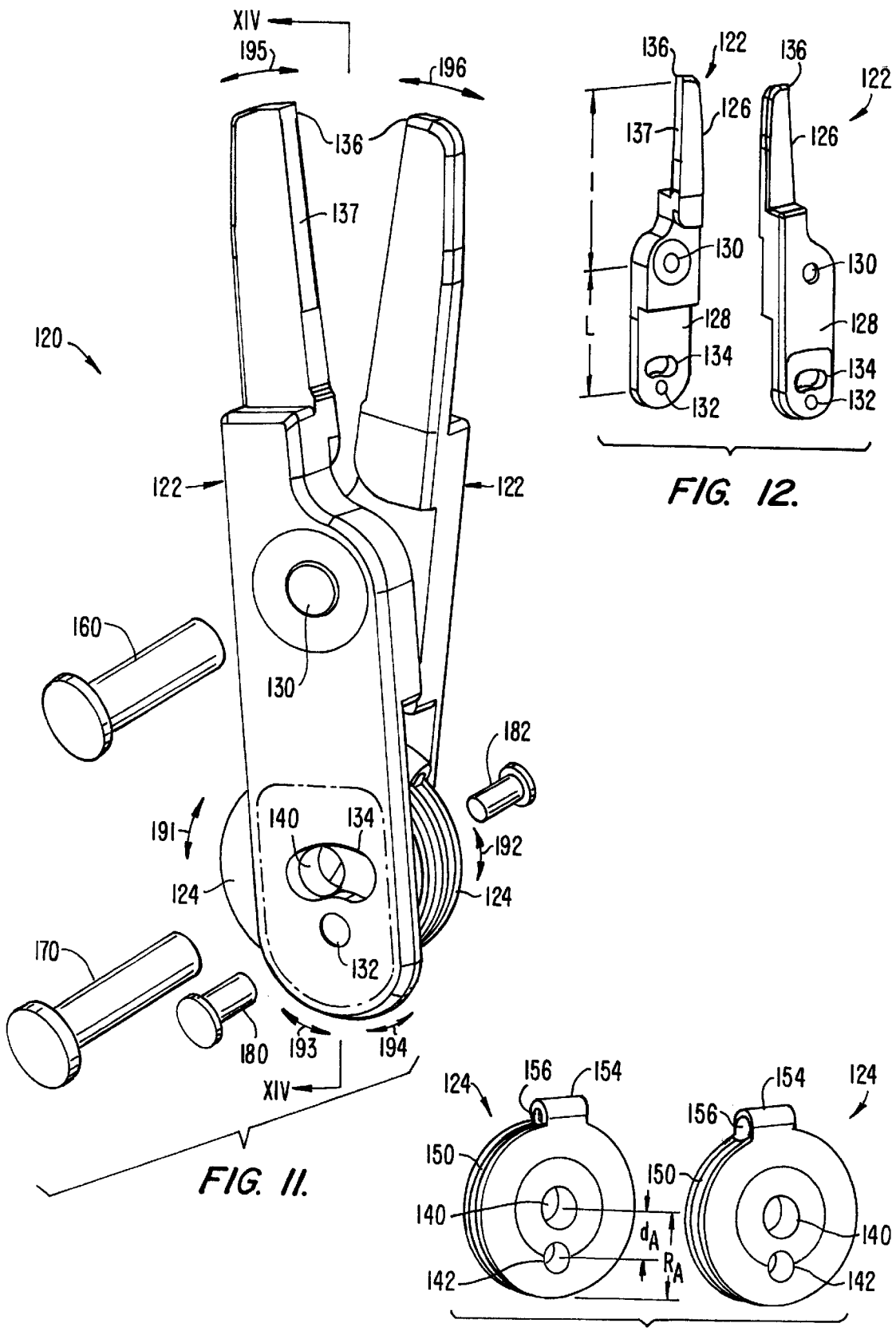

SURGICAL TOOL WITH MECHANICAL ADVANTAGE

CROSS-REFERENCES TO RELATED APPLICATIONS

This application is related to the following patents and patent applications, the full disclosures of which are incorporated herein by reference: PCT International Application No. PCT/US98/19508, entitled "Robotic Apparatus", filed on Sep. 18, 1998, U.S. application Ser. No. 60/111,713, entitled "Surgical Robotic Tools, Data Architecture, and Use", filed on Dec. 8, 1998; U.S. application Ser. No. 60/111,711, entitled "Image Shifting for a Telerobotic System", filed on Dec. 8, 1998; U.S. application Ser. No. 60/111,714, entitled "Stereo Viewer System for Use in Telerobotic System", filed on Dec. 8, 1998; U.S. application Ser. No. 09/398,507, entitled "Master Having Redundant Degrees of Freedom", filed on Sep. 17, 1999, U.S. application Ser. No. 09/399,457, entitled "Cooperative Minimally Invasive Telesurgery System", filed on Sep. 17, 1999; U.S. Provisional Application Ser. No. 09/373,678, entitled "Camera Referenced Control in a Minimally Invasive Surgical Apparatus", filed on Aug. 13, 1999; U.S. Provisional Application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end. effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

Some surgical tools have two working members or fingers which pivot about a common pivotal axis, such as graspers or forceps. The fingers are actuated to exert a gripping force on objects such as tissues. For a clip applier, a gripping force is used to bend a clip loaded in the clip applier and affix the clip onto tissue or the like. An actuation drive arrangement such as a pulley and cable system, a push-pull rod, or the like is provided in the surgical tool to actuate the end effectors. Because the size of the end effector is preferably kept small, existing ways of actuating the end effector may not be easily adaptable for applying the desired gripping force. For instance, in a pulley and cable system, the force transmission is often increased by increasing the size of the pulleys. In minimally invasive robotic surgery, a significant increase in the size of the pulleys used in an end effector is not desirable.

SUMMARY OF THE INVENTION

The present invention is generally directed to robotic surgery methods, devices, and systems. The invention provides an end effector having a mechanical advantage to provide enhanced end effector actuation forces without significantly increasing the size of the tool. In particular, the cross-sectional size of the end effector is kept sufficiently small so that it can be passed through a cannula sleeve to an internal surgical site and manipulated from outside the patient's body. In some embodiments, a pulley and cable mechanism is used to actuate the end effector. The coupling between the pulleys and the fingers of the end effector takes advantage of changes in moment arms for force transfer to avoid or minimize force reduction between the applied cable tensions and the resultant forces at or near the distal tips of the fingers. In specific embodiments, the coupling of the pulleys and fingers results in a force gain.

In accordance to an aspect of the present invention, an end effector arrangement of a minimally invasive surgical instrument includes a first end effector mounting formation having a proximal end portion and a distal end portion which includes a first distal pivot location. The end effector arrangement further includes a second end effector mounting formation having a proximal end portion and a distal end portion which includes a second distal pivot location. The distal end portions of the first and second end effector mounting formations are rotatably coupled together at the first and second distal pivot locations to rotate with respect to each other. Each end effector mounting formation is arranged to carry an end effector element. A first pulley is rotatable about a first center of rotation and has a first force transfer location spaced from the first center of rotation. The proximal end portion of the first end effector mounting formation is rotatably coupled with the first pulley at the first force transfer location to rotate with respect to one another. A second pulley is rotatable about a second center of rotation and has a second force transfer location spaced from the second center of rotation. The proximal end portion of the second end effector mounting formation is rotatably coupled with the second pulley at the second force transfer location to rotate with respect to one another.

In some embodiments, the first and second centers of rotation are aligned, and the first and second pulleys are rotatably coupled together at the centers of rotation to rotate with respect to one another. The first and second end effector mounting formations are rotatably coupled together to move the end effector elements toward one another to contact at a contact position and away from one another generally in a plane of movement.

In a specific embodiment, the first and second force transfer locations are generally aligned in the contact position. The centers of rotation of the first and second pulleys are disposed between the generally aligned force transfer locations and the rotatably coupled first and second distal pivot locations of the end effector mounting formations. The centers of rotation of the first and second pulleys, the first and second force transfer locations, and the first and second distal pivot locations of the end effector mounting formations lie generally on a mid-plane which is perpendicular to the plane of movement when the first and second end effector mounting formations are arranged to position the end effector elements in the contact position.

In accordance with another aspect of the invention, an end effector arrangement of a minimally invasive surgical instrument includes a first finger and a second finger. The first finger includes a proximal end portion having a first finger transfer aperture, a distal end portion, and a first finger pivot hole disposed between the proximal end portion and the distal end portion. The second finger includes a proximal end portion having a second finger transfer aperture, a distal end portion, and a second finger pivot hole disposed between the proximal end portion and the distal end portion. The first pivot hole and the second pivot hole are rotatably coupled for pivoting of the first and second fingers relative to one another. A first pulley is rotatable about a first pulley pivot hole and has a first pulley transfer aperture spaced from the first pulley pivot hole. The first finger transfer aperture of the first finger is rotatably coupled with the first pulley transfer aperture for pivoting of the first finger and the first pulley relative to one another. A second pulley is rotatable about a second pulley pivot hole and has a second pulley transfer aperture spaced from the second pulley pivot hole. The second finger transfer aperture of the second finger is rotatably coupled with the second pulley transfer aperture for pivoting of the second finger and the second pulley relative to one another.

In some embodiments, the first and second finger pivot holes, the first and second pulley pivot holes, and the first and second pulley transfer apertures lie generally on a mid-plane. The first and second finger transfer apertures are disposed on opposite sides of the mid-plane during the full range of pivoting of the first and second fingers relative to one another. In a specific embodiment, the first and second fingers are generally identical, and the first and second pulleys are generally identical.

In accordance with another aspect of the present invention, an end effector arrangement of a minimally invasive surgical instrument includes a first end effector mounting formation and a second end effector mounting formation. The first formation has a proximal end portion and a distal end portion which includes a first distal pivot location. The second formation has a proximal end portion and a distal end portion which includes a second distal pivot location. The distal end portions of the first and second end effector mounting formations are rotatably coupled together at the first and second distal pivot locations to rotate with respect to each other. Each end effector mounting formation is arranged to carry an end effector element. A first force transfer member is rotatable about a first center of rotation by a first applied force normal to a first applied moment arm extending from the first center of rotation. The first force transfer member is coupled with a first transfer location in the proximal end portion of the first end effector mounting formation to transfer a first transfer force to the first transfer location in response to the first applied force. The first transfer force has a first normal force component normal to a first transfer moment arm extending from the first distal pivot location to the first transfer location. The first normal force component is equal to or larger than the first applied force. A second force transfer member is rotatable about a second center of rotation by a second applied force normal to a second applied moment arm extending from the second center of rotation. The second force transfer member is coupled with a second transfer location in the proximal end portion of the second end effector mounting formation to transfer a second transfer force to the second transfer location in response to the second applied force. The second transfer force has a second normal force component normal to a second transfer moment arm extending from the second distal pivot location to the second transfer location. The second normal force component is equal to or larger than the second applied force.

In specific embodiments, the first force transfer member includes a first pulley and the second force transfer member includes a second pulley. The centers of rotation of the first and second pulleys are rotatably coupled together.

In accordance with another aspect of this invention, an end effector arrangement of a minimally invasive surgical instrument includes a first finger and a second finger. The first finger includes a proximal end portion, a distal end portion, and a first finger pivot hole disposed between the proximal end portion and the distal end portion. The second finger includes a proximal end portion, a distal end portion, and a second finger pivot hole disposed between the proximal end portion and the distal end portion. The finger pivot holes are rotatably coupled for pivoting of the first and second fingers relative to one another. A first actuation member is rotatable about a first actuation member pivot hole. The arrangement includes a first mechanism coupled between the first finger and the first actuation member for transferring a first transfer force from the first actuation member to the first finger at a first transfer location in response to a first tangential force applied to the first actuation member. The first tangential force is normal to a radial direction extending radially from the first actuation member pivot hole. The first transfer force is normal to a first finger moment arm measured from the first finger pivot hole to the first transfer location, and is equal to or greater than the first tangential force. A second actuation member is rotatable about a second actuation member pivot hole. The arrangement includes a second mechanism coupled between the second finger and the second actuation member for transferring a second transfer force from the second actuation member to the second finger at a second transfer location in response to a second tangential force applied to the second actuation member. The second tangential force is normal to a radial direction extending radially from the second actuation member pivot hole. The second transfer force is normal to a second finger moment arm measured from the second finger pivot hole to the second transfer location, and is equal to or greater than the second tangential force.

In accordance with another embodiment of the invention, a robotic surgical system includes a robotic arm manipulating a surgical tool holder per instructions received via a processor. A tool is mounted to the tool holder. The tool includes an elongate shaft extending from the tool holder toward a surgical end effector, a drive member movable relative to the shaft to actuate the end effector, and a mechanical advantage mechanism coupling the drive member with the end effector so that an actuation moment applied by the end effector is greater than a drive force transmitted from the drive member to the end effector times the radius of the shaft. The end effector is a clip applier in a specific embodiment.

In accordance with another embodiment of this invention, a robotic surgical system includes a robotic arm manipulating a surgical tool holder per instructions received via a processor, and a tool mounted to the tool holder. The tool includes an elongate shaft extending from the tool holder toward a surgical end effector, a drive member movable relative to the shaft to actuate the end effector, and a mechanical advantage mechanism coupling the drive member with the end effector so that an actuation force applied by the end effector is greater than a drive force transmitted from the drive member to the end effector. In a specific embodiment, the end effector is a clip applier.

Yet another embodiment of the invention relates to a method for performing robotic surgery. The method includes coupling an end effector with an elongate shaft, introducing the end effector into a surgical site, and transmitting a drive force to the end effector. The drive force transmitted to the end effector is multiplied to produce a multiplied force which is greater than the drive force. The multiplied force is applied with the end effector. In specific embodiments, the drive force is multiplied by at least about 1.2, more desirably at least about 2. The end effector may be a clip applier for applying a clip to a target tissue. The end effector may include a pair of working members for manipulating tissue. In a specific embodiment, the end effector has a pair of working members, and applying the multiplied force with the end effector includes holding one of the working members generally fixed and moving the other of the working members relative to the generally fixed working member.

BRIEF DESCRIPTION OF THE DRAWINGS

FIG. 5 is a perspective view of a wrist mechanism in accordance with a preferred embodiment of the invention;

FIG. 6 is a side view of the wrist mechanism shown in FIG. 5 along arrow VI;

FIG. 7 is an end view of the wrist mechanism shown n FIG. 5 along arrow VII;

FIG. 11 is a perspective view of a clip applier end effector with mechanical advantage according to a preferred embodiment of the present invention;

FIG. 12 is an exploded perspective view of the two fingers of the clip applier end effector of FIG. 11;

FIG. 13 is an exploded perspective view of the two pulleys of the clip applier end effector of FIG. 11;

DESCRIPTION OF THE PREFERRED EMBODIMENTS

Figure 1:
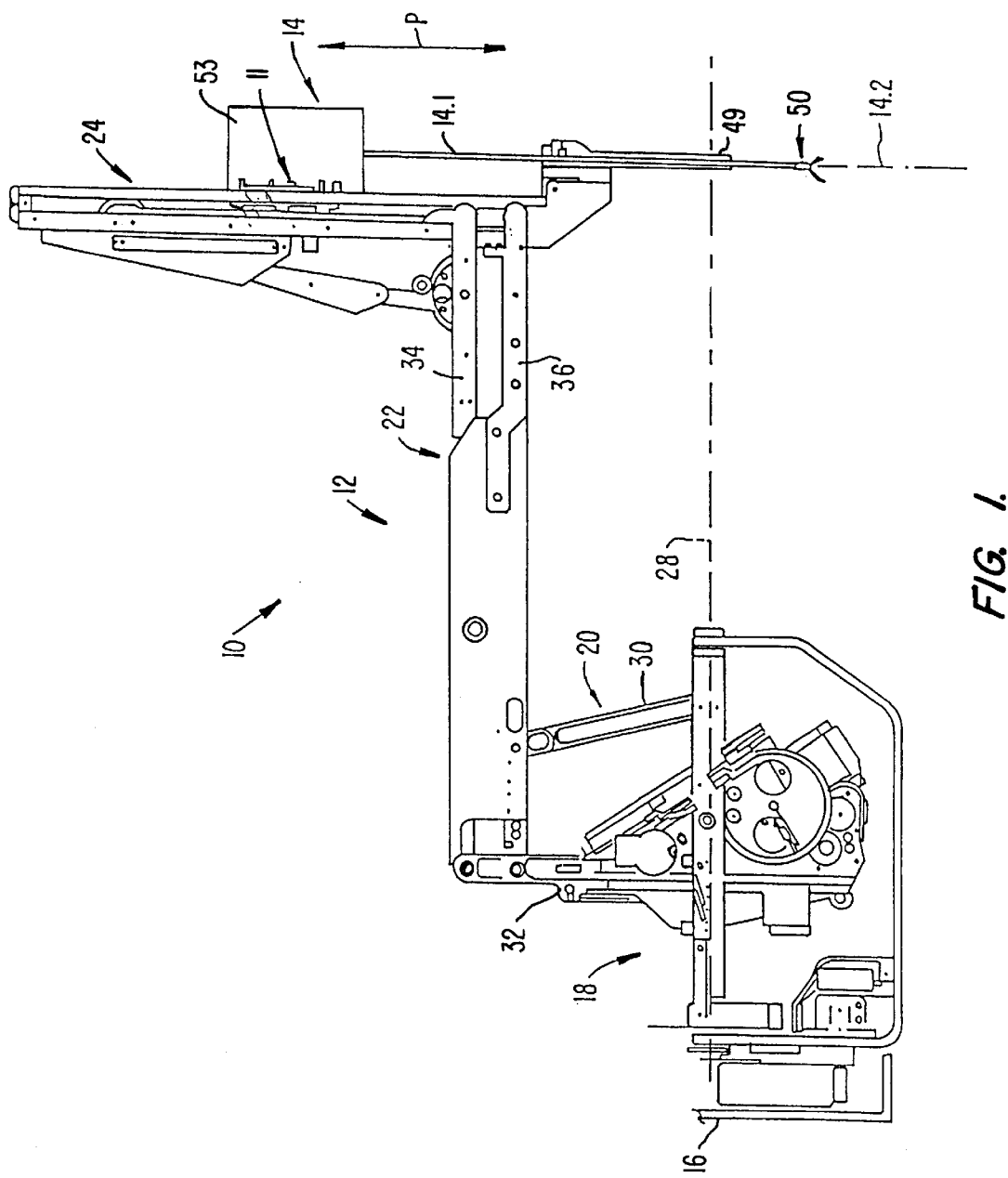
FIG. 1 is a side view of a robotic arm and surgical instrument assembly according to a preferred embodiment of the invention.
Figure 2:
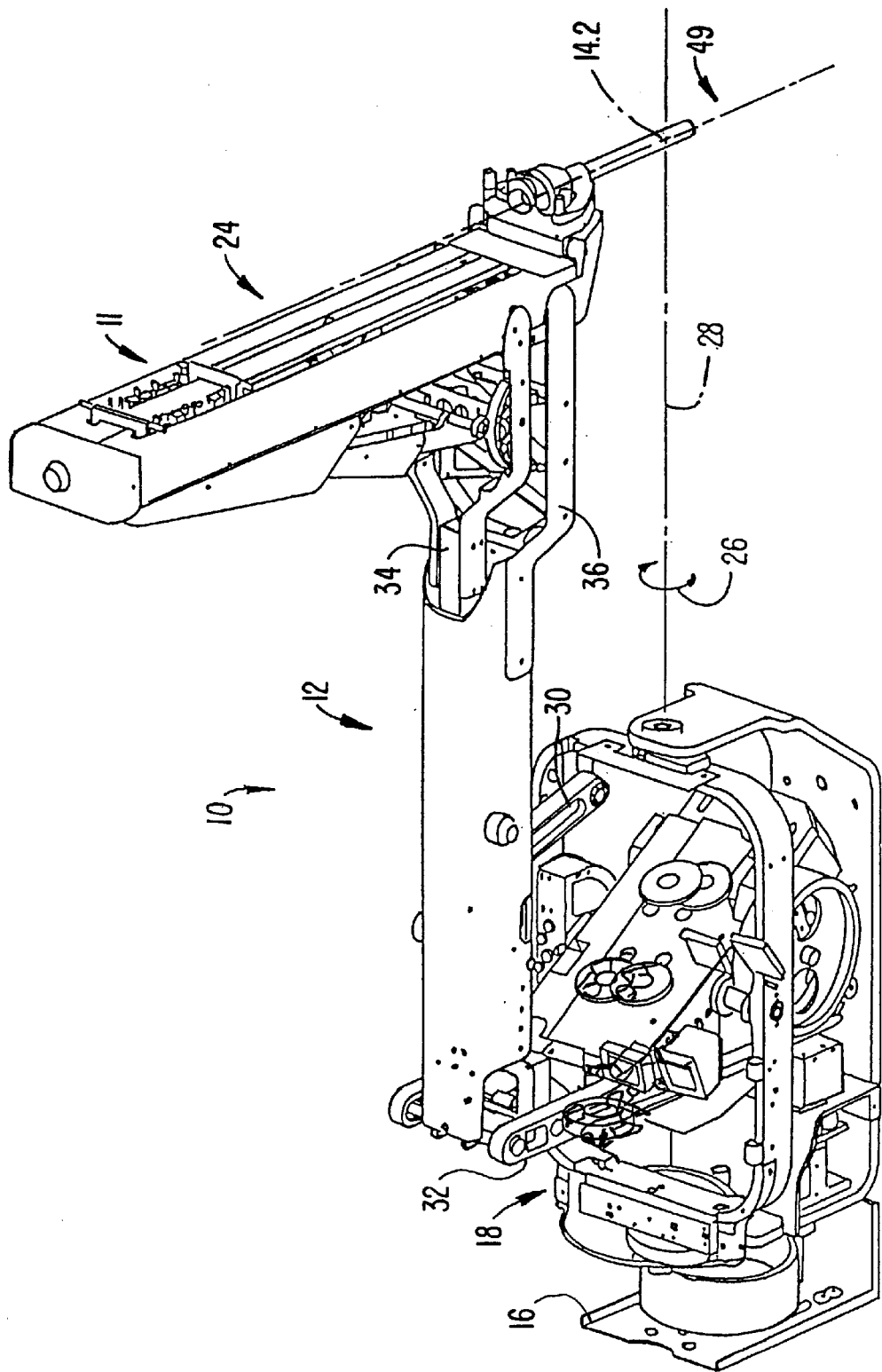
FIG. 2 is a perspective view of the robotic arm and surgical instrument assembly of FIG. 1.
Figure 3:
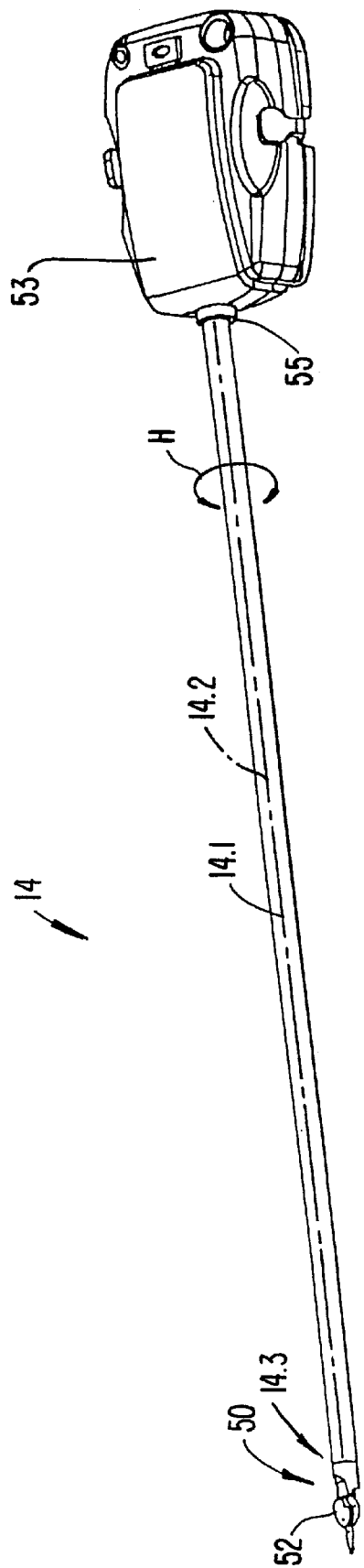
FIG. 3 is a perspective view of a surgical instrument according to a preferred embodiment of the invention.

FIGS. 1 and 2 illustrate a robotic arm and surgical instrument assembly 10. The assembly 10 includes a robotic arm 12 and a surgical instrument 14. FIG. 3 indicates the general appearance of the surgical instrument 14.

The surgical instrument 14 includes an elongate shaft 14.1. A wrist-like mechanism 50 is located at a working end of the shaft 14.1. A housing 53 arranged releasably to couple the instrument 14 to the robotic arm 12 is located at an opposed end of the shaft 14.1. In FIG. 1, and when the instrument 14 is coupled or mounted on the robotic arm 12, the shaft 14.1 extends along an axis indicated at 14.2. The instrument 14 is typically releasably mounted on a carriage 11 which is driven to translate along a linear guide formation 24 in the direction of arrows P. The surgical instrument 14 is described in greater detail herein below.

The robotic arm 12 is typically mounted on a base (not shown) by a bracket or mounting plate 16. The base is typically in the form of a mobile cart or trolley (not shown) which is retained in a stationary position during a surgical procedure.

The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle in the direction of arrows 26 about a pivot axis 28, as shown in FIG. 2. The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to enable the robotic arm to move in a specific manner.

Figure 4:
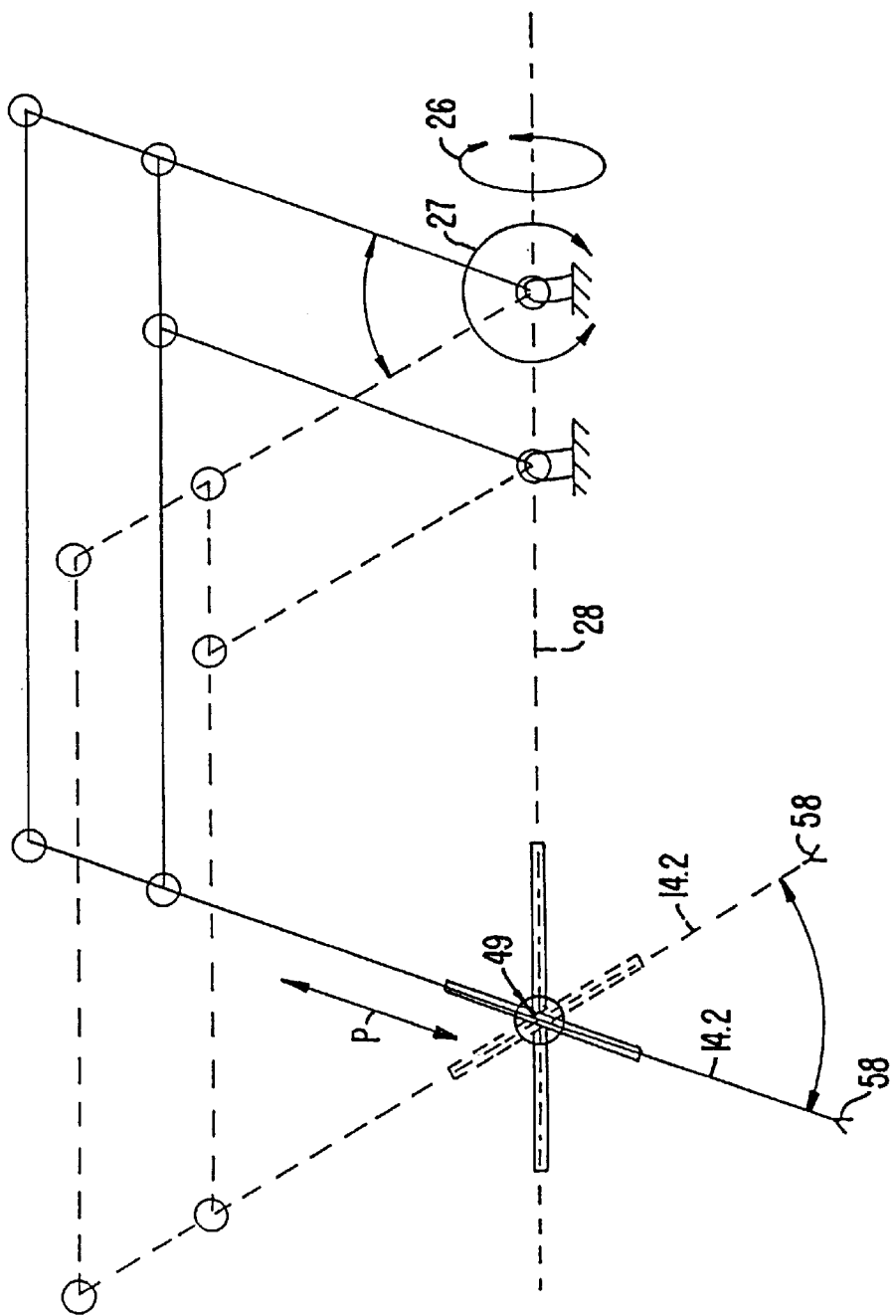
FIG. 4 is a schematic kinematic diagram corresponding to the side view of the robotic arm shown in FIG. 1, and indicates the arm having been displaced from one position into another position.

The movements of the robotic arm 12 is illustrated schematically in FIG. 4. The solid lines schematically indicate one position of the robotic arm and the dashed lines indicate another possible position into which the arm can be displaced from the position indicated in solid lines.

It will be understood that in a preferred embodiment, the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in substantially the same position relative to the stationary cart 300 on which the arm 12 is mounted. In use, the pivot center 49 is typically positioned at a port of entry into a patient's body during an endoscopic procedure when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry. It is to be appreciated that the field of application of the invention is not limited to surgical procedures at internal surgical sites only, but can be used on open surgical sites as well.

As can best be seen in FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27, and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control.

Referring now to FIGS. 5, 6 and 7 of the drawings, a preferred embodiment of the wrist-like mechanism 50 in accordance with the invention will now be described in greater detail. In FIG. 5, the working end of the shaft 14.1 is indicated at 14.3. The wrist-like mechanism 50 includes a rigid wrist member 52. One end portion of the wrist member 52 is pivotally mounted in a clevis 17 on the end 14.3 of the shaft 14.1 by means of a pivotal connection 54. As best seen in FIG. 7, the wrist member 52 can pivot in the direction of arrows 56 about the pivotal connection 54. An end effector, generally indicated by reference numeral 58, is pivotally mounted on an opposed end of the wrist member 52. The end effector 58 is in the form of a clip applier for anchoring clips during a surgical procedure. Accordingly, the end effector 58 has two parts 58.1, 58.2 together defining a jaw-like arrangement.

The end effector 58 is pivotally mounted in a clevis 19 on an opposed end of the wrist member 52, by means of a pivotal connection 60. Free ends 11, 13 of the parts 58.1, 58.2 are angularly displaceable about the pivotal connection 60 toward and away from each other as indicated by arrows 62, 63 in FIG. 6. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58 is, as a whole, angularly displaceable about the pivotal connection 60, as indicated in dashed lines in FIG. 6.

Figure 8:
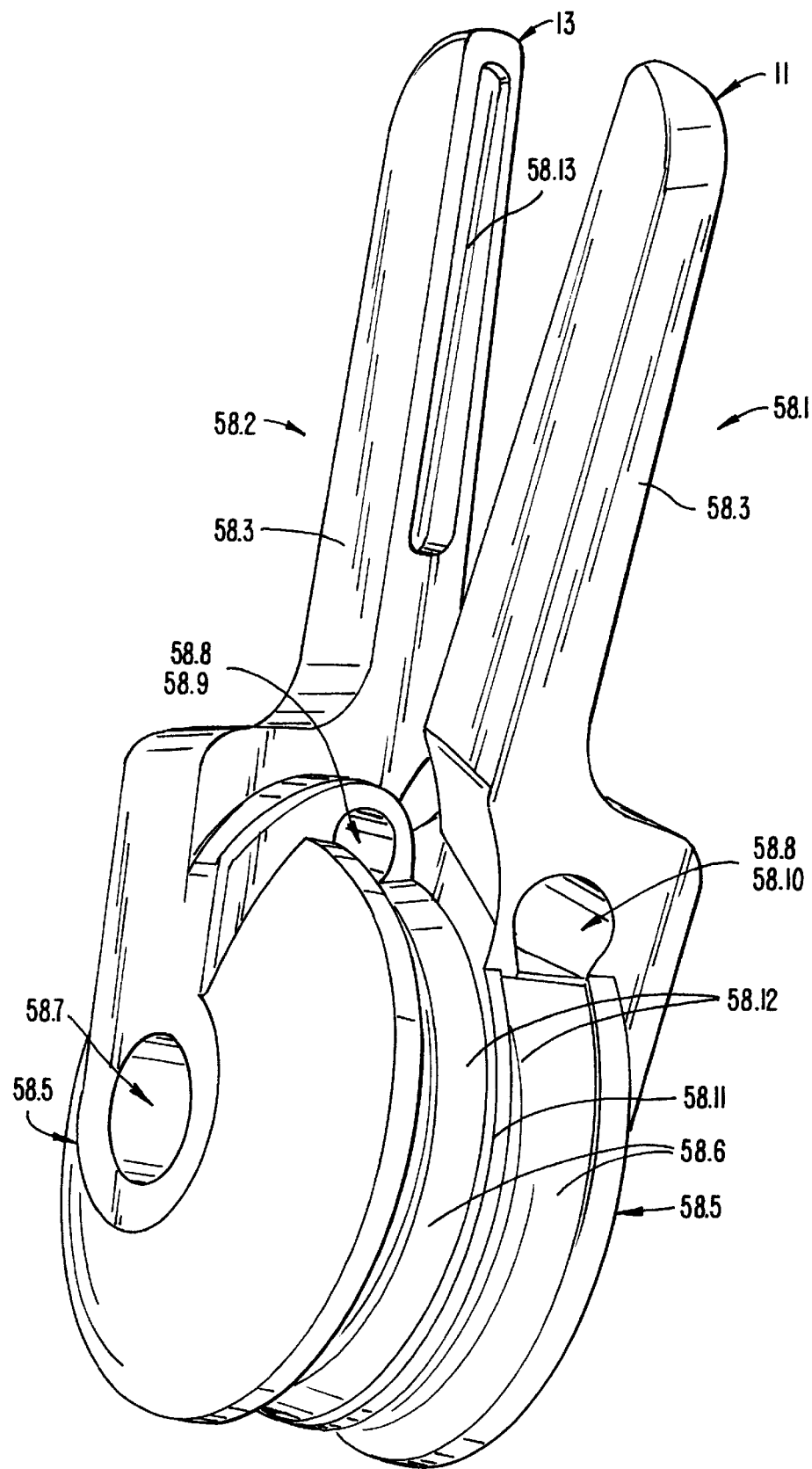
FIG. 8 is a perspective view of a clip applier end effector according to one embodiment.
Figure 9:
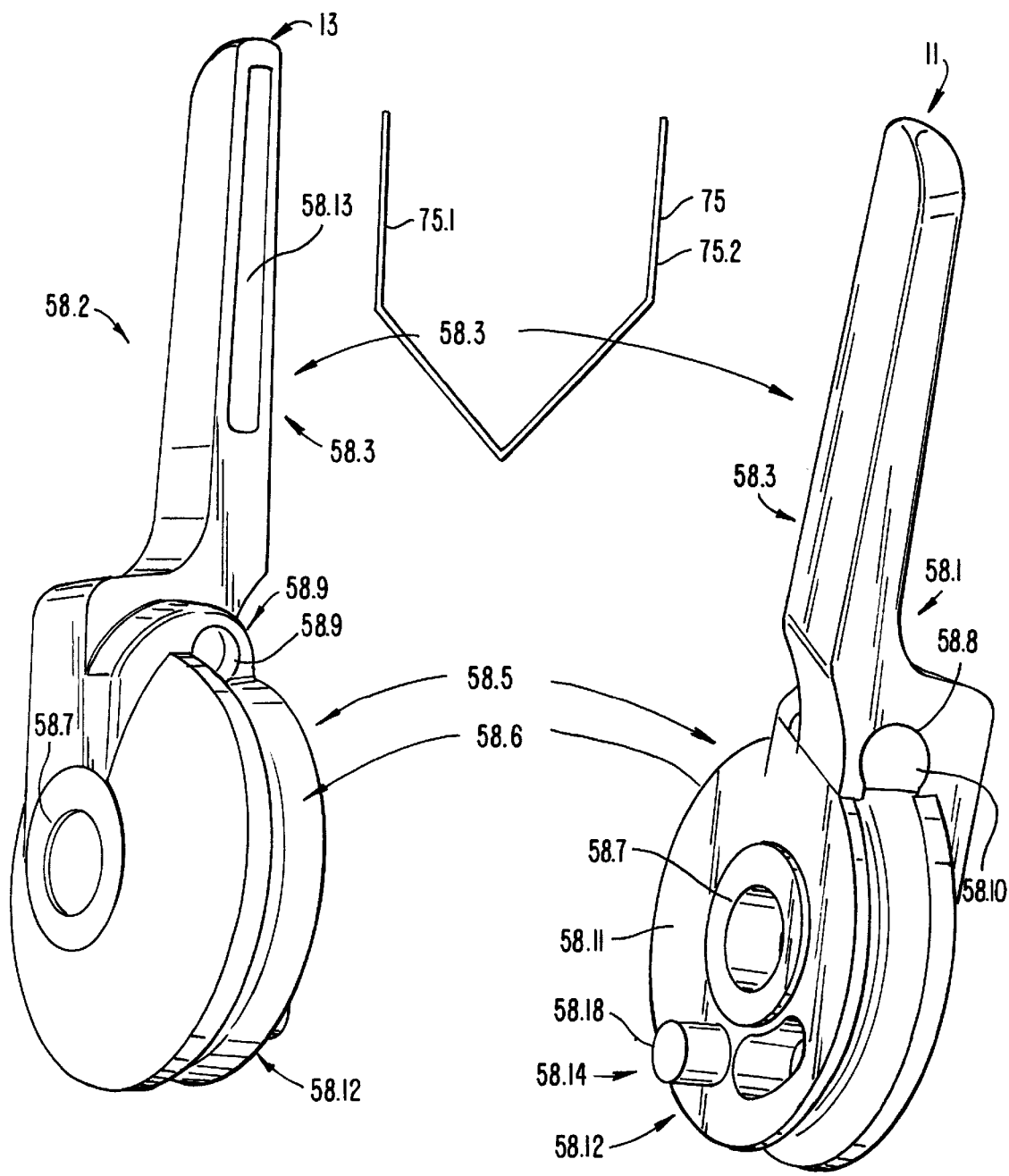
FIG. 9 is an exploded view of the clip applier end effector shown in FIG. 8.

FIGS. 8 and 9 show in greater detail a preferred clip applier end effector 58 for the tool 14 of FIG. 5. The parts 58.1, 58.2 of the end effector 58 typically are preferably the same so as to keep production costs low. Accordingly, the parts 58.1, 58.2 each include an elongate finger portion or end effector element 58.3. The finger portion 58.3 is integrally formed with an end effector mounting formation in the form of, e.g., a pulley portion 58.5. The pulley portion 58.5 defines a circumferentially extending channel 58.6 in which an elongate element in the form of, e.g., an activation cable, is carried.

The pulley portion 58.5 includes an axially extending, centrally disposed hole 58.7 through which a pivot pin of the pivotal connection 60 extends. A generally circumferentially directed hole 58.8 extends through a nape region of the finger portion 58.3 and generally in register with the circumferentially extending channel 58.6. The hole 58.8 has a first portion 58.9 and a second portion 58.10 having a diameter greater than the first portion 58.9. In use, the activation cable has a thickened portion along its length which seats in the hole portion 58.10, the rest of the activation cable then extending along the channel 58.6 in opposed directions. The thickened portion is crimped in its seated position in the hole portion 58.10 so as to anchor the cable in the hole 58.8. It will be appreciated that a greater force is necessary to clamp the free ends together when gripping an object therebetween, than that which is required to open the free ends 11, 13. Thus, the thickened portion of the cable is urged against an annular stepped surface between the hole portion 58.9 and the hole portion 58.10, when the free ends 11, 13 are urged into a closed condition. The part 58.1, 58.2 has an operatively inwardly directed face 58.11 which rides against the face 58.11 of the other one of the parts 58.1, 58.2.

As best seen in FIG. 6, the wrist member 52 is flanked by two sets of pulleys 64, 66 which are coaxially positioned on the pivotal connection 54 and in the clevis 17 at the end 14.3 of the shaft 14.1. Two further sets of pulleys 68, 70 are rotatably mounted on opposed sides of the wrist member 52. Each pulley of the set of pulleys 68 on the one side of the wrist member 52 is generally co-planar with an associated pulley of the pulley set 66. Furthermore, each of the pulleys 68 is positioned such that its circumference is in close proximity to the circumference of its associated pulley of the pulley set 66. A similar arrangement exists for each pulley of the pulley set 70 on the other side of the wrist member and its associated pulley of the pulley set 64. Thus, the circumferentially extending channel formation of each pulley of the pulley sets 68, 70 and their associated pulleys of the pulley sets 64, 66 define between each of them a space 72 through which an activation cable can snugly pass.

A plurality of elongate elements, e.g., cables, are used to effect movement of the wrist mechanism 50 and end effector 58. As seen in FIG. 7, two cables C1, C2 are anchored on the parts 58.1, 58.2, respectively, to effect movement of the parts 58.1, 58.2 independently in directions 62, 63 or as a whole (FIG. 6).

Cable C1 rides over an outer pulley of the pulley set 64, an outer pulley of the pulley set 70, over part of circumferential channel 58.6 of the pulley portion 58.5 of the part 58.2 of the end effector 58, through the hole 58.8, again along part of the circumferential channel 58.6 of the pulley portion 58.5, over an outer pulley of the pulley set 68 and over an outer pulley of the pulley set 66. Similarly, cable C2 rides over an inner pulley of the pulley set 64, over an inner pulley of the pulley set 70, along the circumferential channel 58.6 of the part 58.1 of the end effector 58, through the hole 58.8 of the part 58.1, again along the circumferential channel 58.6 of the pulley portion 58.5, over an inner pulley of the pulley set 68 and over an inner pulley of the pulley set 66. The cables C1, C2 pass from the wrist mechanism 50 through appropriately positioned holes 47 in the base region of the clevis 17 (FIG. 5), and internally along the shaft, toward the housing 53 (FIG. 3).

In use, a clip 75, as indicated in FIG. 9, is positioned between the finger portions 58.3. Opposed limbs 75.1, 75.2 of the clip 75 are positioned in longitudinally extending recesses or seats 58.13 in each of the finger portions 58.1, 58.2. It is important that the clip is securely seated in the clip applier 58 until the clip applier is caused to anchor the clip in position. If the clip 75 is not securely seated, the clip 75 could become dislocated from the clip applier 58. In such a case, valuable time could be lost in trying to find and recover the clip 75 from the surgical site. To cause the clip 75 to seat securely on the clipper appliers 58, the portions 58.1 58.2 are biased or urged in a closing direction so as to clamp the clip 75 in the opposed seats or recesses 58.13. The biasing or urging arrangement to cause such clamping of the clip 75 in the seats 58.13, as well as the mechanisms for operating the clip applier end effector 58, is discussed in greater detail in U.S. application Ser. No. 09/398,958 (Attorney Docket No. 17516-004410), entitled "Surgical Tools for Use in Minimally Invasive Telesurgical Applications", filed on Sep. 17, 1999.

Figure 9A:
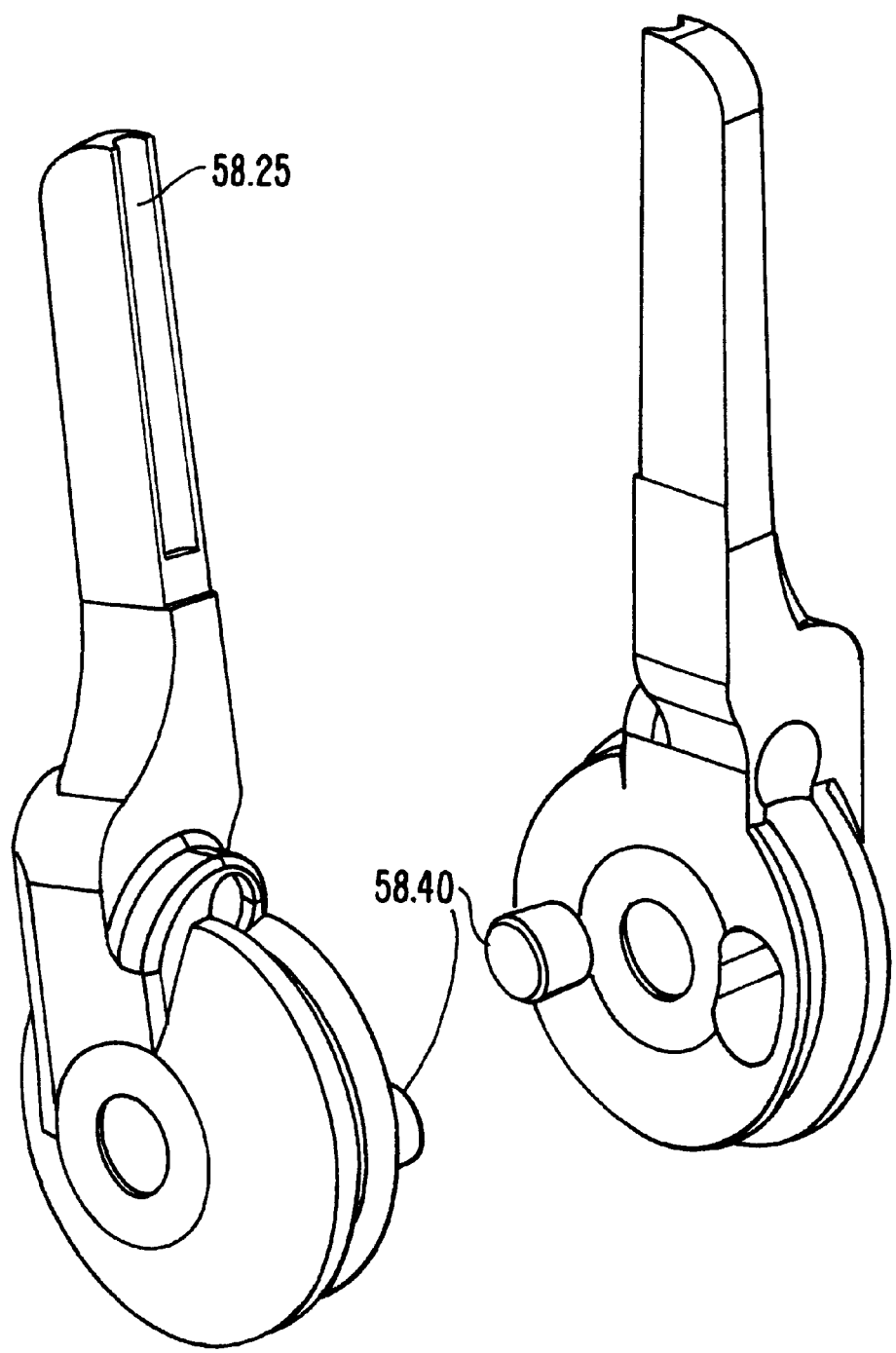
FIG. 9A is an exploded perspective view of a clip applier end effector according to another embodiment.

As discussed in the application entitled "Surgical Tools for Use in Minimally Invasive Telesurgical Applications", a clip applier may also be constructed without such a biasing mechanism so as to hold a loaded clip by means of friction alone. In such case, each finger member of the clip applier would have an associated mechanical stop or pin 58.40. Such a mechanism is shown in FIG. 9A. This pair of mechanical stops would physically prevent the two finger portions from opening beyond a certain angle. To use friction to maintain a clip in position between the finger members upon loading, the finger members preferably would have a maximum open angle slightly less—by fractions of a degree—than the angle of the clip to be loaded. The finger members are opened with a low-torque software command that instructs the fingers to occupy a position past the mechanical stops, thereby guaranteeing that each member will come to rest at its mechanical stop and be urged against the stop. A low-torque command, preferably in the order of only several hundredths of an N-m, is preferred for this step to ensure correct positioning of the finger members without damaging the mechanism used to position the members against the stops. Upon loading, the inherent biasing force in the clip itself can help to hold the clip in place. For this mechanical stop embodiment, slots 58.13 may have an open distal portion to form a channel 58.25 in FIG. 9A, so that the clip can slide between the finger members without becoming so compressed that it can no longer bias against the finger members and cannot be loaded. Once loaded, the clip applier can be closed with a much higher torque command—perhaps 5 to 10 times as much as the torque used to open the finger members—to provide the force necessary to apply the clip around the tissue of interest.

Figure 10:
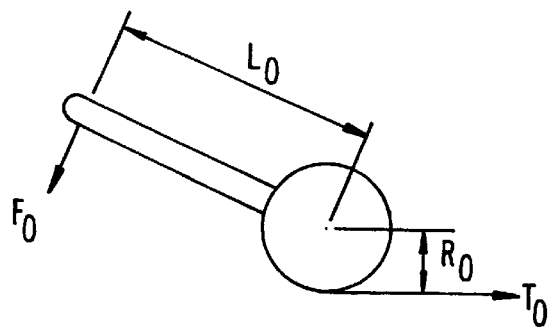
FIG. 10 is a simplified sketch schematically illustrating the force transmission provided by the clip applier end effector of FIG. 8.

To apply the clip 75 to a target tissue, for example, the pulley and cable system converts the applied cable tensions into resultant forces on the finger portions 58.3 of the first and second members 58.1, 58.2, causing them to close so as to bend the clip 75. Referring to FIG. 10, a force reduction occurs in the clip applier 58 of FIGS. 8 and 9, as represented by the following equation:

$$F_0 = (R_0/L_0)*T_0,$$

where $T_0$ is the cable tension of the activation cables, $R_0$ is the radius of the pulley portion 58.5, $L_0$ is the distance from the center of the hole 58.7 of the pulley portion 58.5 to the tip (11 or 13) of the finger portion 58.3, and $F_0$ is the force at the tip (11 or 13) of the finger portion 58.3.

The force reduction results because $R_0/L_0$ is less than 1, and is typically less than ½. For a given force $F_0$ necessary to bend the clip 75, a significantly higher tension $T_0$ is required. The force reduction imposes a high demand on the cables C1, C2 as well as on the actuation mechanism for the cables.

Another preferred embodiment of an end effector 120 according to the present invention shown in FIGS. 11–15 incorporates a mechanical advantage to generate significantly larger gripping forces from the tension forces applied by the activation cables C1, C2. In a specific embodiment, the end effector 120 is intended to replace the two parts 58.1, 58.2 of the end effector 58 of FIGS. 8 and 9, and to be used with the wrist mechanism 52 of FIGS. 5–7. As illustrated in FIGS. 11—15, the end effector 120 includes a pair of generally identical fingers 122 and a pair of generally identical pulleys 124. Although identical fingers 122 and pulleys 124 are typically used to keep production costs down, it is understood that other embodiments may include differently sized and configured fingers and pulleys.

As best seen in FIG. 12, each finger 122 includes a grip portion 126 integrally formed with an attachment portion 128. Disposed between the grip portion 126 and the attachment portion 128 is a finger pivot hole 130. The attachment portion 128 includes a finger transfer aperture 132 and a finger slot 134. The grip portion 126 includes a tip 136, and a longitudinally extending recess or seat 137 for holding the clip 75. The attachment portion 128 is an end effector mounting formation for the grip portion 126. In alternate embodiments, the grip portion 126 may be releasably mounted on the attachment portion 128.

The distance between the center of the finger pivot hole 130 and the center of the finger transfer aperture 132 is $L_1$ for one finger 122 and is $L_2$ for the other finger 122. The distance between the center of the finger pivot hole 130 and the tip 136 is $l_1$ for one finger 122 and is $l_2$ for the other finger 122. In the specific embodiment where the two fingers 122 are identical, $L_1=L_2=L$, and $l_1=l_2=l$.

As shown in FIG. 13, the pulley 124 includes a pulley pivot hole 140 in the center and a pulley transfer aperture 142 disposed between the pulley pivot hole 140 and the edge. The pulley 124 further includes a circumferentially extending channel 150 in which an activation cable (C1 or C2) is carried for moving the pulley 124, and a generally circumferentially directed tube 154 having a bore 156 generally in register with the circumferentially extending channel 150.

The radius of one pulley 124 is $R_1$ and the radius of the other pulley 124 is $R_2$. The distance between the center of the pulley pivot hole 140 and the center of the pulley transfer aperture 142 is $d_1$ for one pulley and is $d_2$ for the other pulley. In the specific embodiment where the two pulleys are identical, $R_1=R_2=R_A$, and $d_1=d_2=d_A$. The radius R typically is approximately equal to the radius of the elongate shaft 14.1 which supports the end effector 120.

Figures 14, 15:
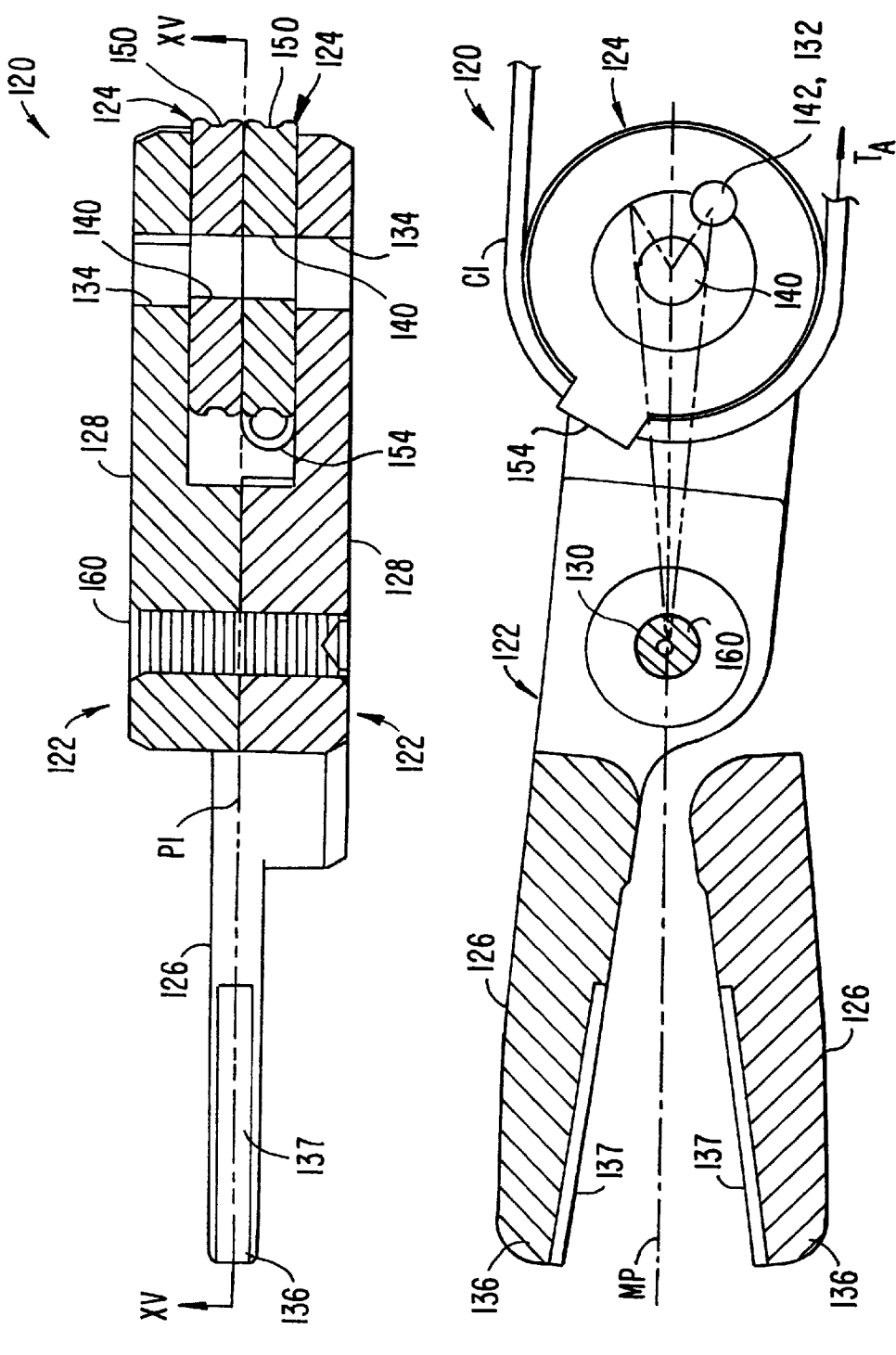
FIG. 14 is a cross-sectional view of the clip applier end effector of FIG. 11 along XIV—XIV.
FIG. 15 is a cross-sectional view of the clip applier end effector of FIG. 11 along XV—XV.

When assembled as shown in FIGS. 11 and 14, a finger pivot pin 160 extends through the finger pivot holes 130 to form a finger pivotal connection for the two fingers 122. A pulley pivot pin 170 extends through the pulley pivot holes 140 of the pulleys 124 and the finger slots 134 of the fingers 122 to form a pulley pivotal connection for the pulleys 124. The finger 122 and pulley 124 on one side of the end effector 120 are coupled together to form a finger-pulley pivotal connection by a first transfer pivot pin 180 extending through the finger transfer aperture 132 of the finger 122 and the pulley transfer aperture 142 of the pulley 124. The finger 122 and pulley 124 on the other side of the end effector 120 are similarly coupled together by a second transfer pivot pin 182 to form another finger-pulley pivotal connection.

In this embodiment, the pulleys 124 and fingers 122 are arranged such that the pulley pivot holes 140 of the pulleys 124 are disposed generally between the pulley transfer apertures 142 and the finger pivot holes 130. In a specific embodiment, the pulley pivot holes 140, pulley transfer apertures 142, finger transfer apertures 132, and finger pivot holes 130 all lie generally close to a mid-plane MP (FIG. 15) when the tips 136 of the finger portions 126 are in contact in a closed or contact position. Although pulleys and cables are used in this embodiment, other activating mechanisms such as push/pull rods could be used.

In operation, the pulleys 124 are pulled by the activation cables (e.g., $C_1$ and $C_2$ in FIG. 7) to pivot relative to the pulley pivotal connection at the pulley pivot pin 170 in directions indicated by arrows 191, 192 in FIG. 11. The pivoting of the first pulley 124 in directions 191 causes the transfer pivot pin 180 to rotate relative to the pulley pivot pin 170 and to produce pivoting of the first finger 122 relative to the pulley 124, thereby causing the proximal end of the first finger 122 to move in directions indicated by arrows 193. The pivoting of the second pulley 124 in directions 192 causes the transfer pivot pin 182 to rotate relative to the pulley pivot pin 170 and to produce pivoting of the second finger 122 relative to the second pulley 124, thereby causing the proximal end of the second finger 122 to move in directions indicated by arrows 194.

The movement of the two fingers 122 by the transfer pivot pins 180, 182 produces a pivoting motion of the fingers 122 relative to the finger pivotal connection at the finger pivot pin 160. For the first finger 122 with movement in directions 193 at the proximal end, the distal tip 136 pivots in directions indicated by arrows 195. The distal tip 136 of the second finger 122 pivots in directions indicated by arrows 196 in response to movement in directions 194 at the proximal end. For the embodiment shown, the relative movements of the pulleys 124 and fingers 122 lie generally in a plane of movement P1 (FIG. 14), which is perpendicular to the mid-plane MP (FIG. 15).

The finger slots 134 provide room for the fingers 122 to maneuver around the pulley pivot pin 170 during pivoting of the fingers 122 to avoid interference. In the embodiment shown in FIG. 1, the finger slots 134 are shaped to match the movement of the pulley pivot pin 170 relative to the fingers 122. As a result, the finger slots 134 serve to guide movement of the pulley pivot pin 170 relative to the fingers 122, and define the limits for the angular rotation therebetween. In alternative embodiments, the finger slots 134 may be replaced by openings that are sized and shaped differently and that serve only to avoid interfering with movement of the pulley pivot pin 170 relative to the fingers 122 without providing a guiding function for the pin 170. There is sufficient constraint among the pulleys 124 and fingers 122 to form a determinate mechanism, so that no guiding of the pulley pivot pin 170 relative to the fingers 122 by the finger slots 134 is needed.

To operate this particular embodiment, the fingers preferably are driven to open so that the pin 170 hits the end of the slot 134, so as to reach a mechanical limit and occupy an "open" angle. Opening in this manner is typically accomplished with a low-torque command, so as not to damage the mechanism, as previously described for the "mechanical stop" clip applier. In this position, the finger members are ready to receive a clip with a slightly larger than the fingers' "open" angle, and are able to hold the clip through friction alone without need for a biasing mechanism and/or slot arrangement (although such may be used if desired), all as previously described.

In this particular "mechanical advantage" embodiment of the clip applier, the pin 170 is preferably farther removed from the center of rotation 130 than the corresponding pin 58.40 in the clip applier without a mechanical advantage mechanism (e.g., shown in FIG. 9A). This, in turn, means that the ratio of this distance to the distance between the center of rotation 130 and the distalmost portions of the end effector fingers is greater than before, approaching a ratio of 1:1. As this ratio of distances increases in this manner, the effect of a slight mispositioning of the pin relative to the effect on the maximum angular opening of the fingers is decreased. Therefore, to decrease manufacturing tolerances, it is preferable to maintain this distance ratio as large as practical.

Figure 16:
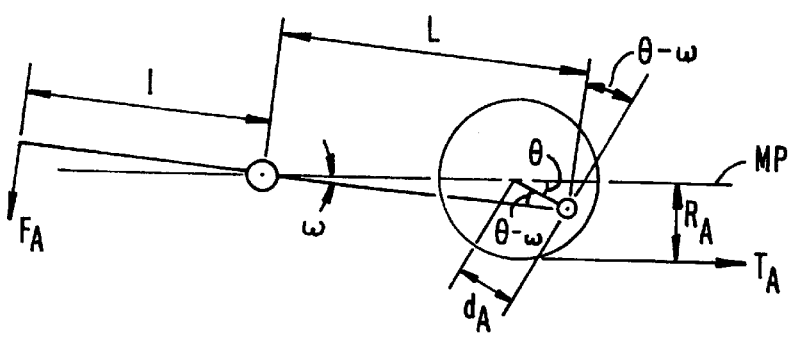
FIG. 16 is a simplified sketch schematically illustrating the force transmission provided by the clip applier end effector of FIG. 11.

The end effector 120 provides a mechanical advantage, as best illustrated in FIGS. 15 and 16. When a tension $T_A$ is applied to the activation cable $C_1$ (only partially shown) at the radius $R_A$ from the center of the pulley 124, it causes a moment of $T_A*R_A$ with respect to the center of the pulley pivot hole 140 of the pulley 124. This moment is transferred from the pulley 124 to the proximal end of the finger 122 via the transfer pivot pin (180 or 182) extending through the pulley transfer aperture 142 of the pulley 124 and the finger transfer aperture 132 of the finger 122. The moment that is transferred to the finger 122 is $T_A*R_A$, which translates into a transfer force on the finger 122 of $T_A*R_A/d_A$, where $d_A$ is the moment arm distance from the center of the pulley pivot hole 140 to the centers of the rotatably coupled pulley transfer aperture 142 and finger transfer aperture 132.

The force $T_A*R_A/d_A$ produces a moment in the finger 122 which pivots relative to the finger pivot pin 160 at the finger pivot hole 130. The moment arm distance from the finger pivot hole 130 to the finger transfer aperture 132 is L. The component of the transfer force which is normal to the moment arm L is $(T_A*R_A/d_A) \cos(\theta-\omega)$. When the clip 75 is loaded in the clip applier 120 but just prior to bending, $\theta$ is the angle between a line extending from the pulley pivot hole 140 to the finger transfer aperture 142 and the mid-plane MP, and $\omega$ is the angle between a line extending from the finger pivot hole 160 to the pulley transfer aperture 142 and the mid-plane MP, as shown in FIG. 16. It is appreciated that (θ−ω) will typically be very small for the clip applier end effector 120, so that cos(θ−ω) will typically be approximately equal to 1.

The moment in the finger 122 which results from the force $(T_A*R_A/d)\cos(\theta-\omega)$ at the moment arm of L is $L*(T_A*R_A/d_A)\cos(\theta-\omega)$. This moment exerts a force near the tip 136 of the grip portion 126 of the finger 122 disposed at the distance l from the finger pivot hole 130. This force $F_A$ is:

$$F_A = T_A(R_A/d_A)(L/l)\cos(\theta-\omega),$$

where $T_A$ is the cable tension of the activation cable;

$R_A$ is the radius of the pulley 124;

$d_A$ is the distance between the center of the pulley pivot hole 140 and the center of the pulley transfer aperture 142;

L is the distance between the center of the finger transfer aperture 132 and the center of the finger pivot hole 130;

l is the distance between the center of the finger pivot hole 130 and the tip 136;

θ is the angle between a line extending from the pulley pivot hole 140 to the pulley transfer aperture 142 and the mid-plane MP prior to bending of the clip 75; and ω is the angle between a line extending from the finger pivot hole 160 to the finger transfer aperture 132 and the mid-plane MP prior to bending of the clip 75.

The ratio $R_A/d_A$ is greater than 1. In specific embodiments, the ratio $R_A/d_A$ is at least about 2. The quantity cos(θ−ω) is typically equal to about 1. The ratio L/l can be smaller than, equal to, or greater than 1, but is typically approximately equal to 1. As a result, $F_A$ is typically greater than $T_A$, representing a force gain. Further, because l is typically greater than $R_A$, the apparatus provides a moment gain as well ($F_A l > T_A R_A$).

In a specific example, $R_A=0.15$ inch, $d_A=0.09$ inch, L=0.4 inch, l=0.52 inch, and (θ−ω)=12°, so that $F_A=1.22\ T_A$. In general, the ratio $F_A/T_A$ is desirably at least approximately 1, and more desirably greater than about 1.

When compared with the end effector 58 of FIGS. 8–9, the improvement in force conversion in the end effector 120 of FIGS. 11–16 is evident:

$$F_A/F_O = (T_A/T_O)(L_O/R_O)(R_A/d_A)(L/l)\cos(\theta-\omega).$$

If the same tension is applied so that $T_A=T_O$, and both end effectors have the same pulley radius so that $R_A=R_O$, then $$F_A/F_O = (L_O/d_A)(L/l)\cos(\theta-\omega).$$

Assuming (L/l) cos(θ−ω)≈1, then $F_A/F_O≈(L_O/d_A)$, which can typically range from about 4 to about 10 or higher. This represents a significant improvement in force transmission for the end effector 120.

It will be appreciated that the end effector with mechanical advantage can be used in any surgical tool having two members or fingers which pivot about a common pivotal axis, such as forceps, pliers for use as needle drivers, or the like.

For the same cable tension or other activation force, the present invention can produce a closing force between end effector fingers about two to ten or more times greater (depending on the particular geometry of the mechanical advantage mechanism used) than the closing force of the clip applier embodiments lacking such a mechanical advantage mechanism. It may be, however, that for a particular cable tension, not all of the closing force resulting from the mechanical geometry is required to perform a particular task (e.g., applying a clip to tissue during endoscopic or other surgery). If less than the maximum closing force is desired, the amount of force used to activate the mechanical advantage arrangement can be reduced by, e.g., reducing the tension of the particular cables used in the preferred embodiment. Decreasing cable tension increases the usable life of both cables and components, due to the decreased wear and tear on the mechanism. Reductions in cable tension of 20%, for example, have easily been achieved, although further reductions would be quite possible depending upon how small a closing force is desired.

The above-described arrangements of apparatus and methods are merely illustrative of applications of the principles of this invention and many other embodiments and modifications may be made without departing from the spirit and scope of the invention as defined in the claims.

For instance, although the end effector 120 has two movable fingers 122 that are movable relative to one another, one of the fingers 122 may be generally fixed and unmovable in an alternate embodiment. The mechanical advantage is realized using the same mechanism by manipulating the pulleys 124 to move the movable finger relative to the unmovable finger.

Figure 17:
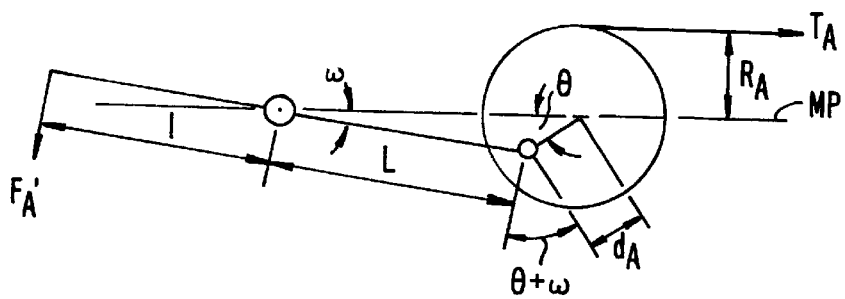
FIG. 17 is a simplified sketch schematically illustrating the force transmission provided by a clip applier end effector with mechanical advantage according to another preferred embodiment of the invention.

In another preferred embodiment, the pulleys 124 and fingers 122 can be arranged such that the rotatably coupled pulley transfer apertures 142 and finger transfer apertures 132 are disposed generally between the pulley pivot holes 140 and the finger pivot holes 130, as illustrated schematically in the simplified sketch in FIG. 17. In this embodiment, the resultant force at the tip 136 is:

$$F_A' = T_A(R_A/d_A)(L/l)\cos(\theta-\omega).$$

The difference between the configurations of FIG. 17 and FIG. 16 is that the component of the transfer force $T_A*R_A/d_A$ (transferred from the pulley 124 to the finger 122) which is normal to the moment arm L of the finger 122 is $(T_A*R_A/d_A)\cos(\theta+\omega)$ in FIG. 17 due to the difference in geometry. The quantity cos(θ+ω) is smaller than the quantity cos(θ−ω), and is about 0.9 for a typical clip applier end effector. The mechanical advantage is reduced by about 10%, but still represents a significant improvement over the clip applier 58 of FIGS. 8–9.

In addition, although a pulley and cable system is used to transfer the applied tension to the fingers 122 to effect the gripping action, other force transfer mechanisms can be used instead to produce the mechanical advantage. Moreover, although the pulley pivot holes 140 of the two pulleys 124 are aligned and coupled together by the pulley pivot pin 170 in FIG. 11, the pulleys 124 may alternatively be independent mounted rotatably on the wrist mechanism 52.

Figure 18:
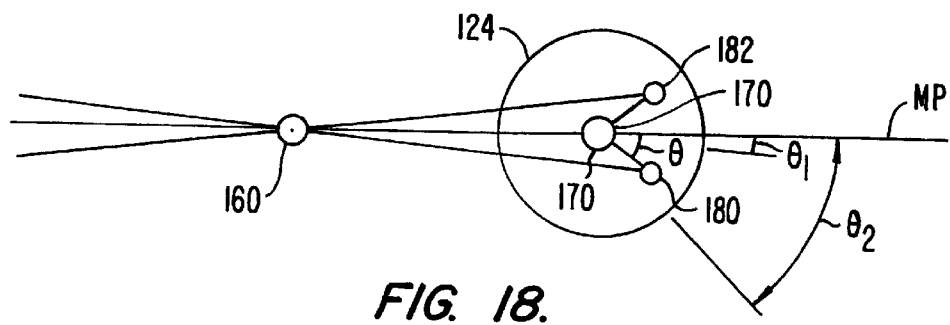
FIG. 18 is a simplified sketch schematically illustrating a clip applier end effector with mechanical advantage according to another preferred embodiment of the invention.

FIG. 18 shows a simplified schematic illustration of another embodiment of the end effector which is configured to provide movement of the transfer pivot pin 180 angularly with the angle θ ranging from $\theta_1$ to $\theta_2$ with respect to the mid-plane MP. The other transfer pivot pin 180 is disposed on the other side of the mid-plane MP. The angle θ is greater than zero. In a preferred embodiment, $\theta_1$ is about 10° and $\theta_2$ is about 60°. The range of the angle θ can be restricted to these angles, for example, by configuring the finger slots 134 to limit the range of relative angular displacement between the pulley pivot pin 170 and the transfer pivot pins 180, 182.

The embodiment of FIG. 18 differs from the embodiment shown in FIG. 16 in the range of the angle θ. In FIG. 16, the range of the angle θ includes zero at the mid-plane MP, and is typically between about 15° and −10°. When θ is zero, the finger pivot pin 160, pulley pivot pin 170, and transfer pivot pins 180, 182 are aligned with the mid-plane MP. At this point, the end effector 120 encounters a singularity where the fingers 122 are no longer held firmly in place. The embodiment illustrated in FIG. 18 avoids the singularity. Although the increase in the angle θ diminishes the mechanical advantage, the reduction is typically no more than 50% which still represents a substantial improvement in force transmission over previous end effectors.

The scope of the invention should, therefore, be determined not with reference to the above description, but instead should be determined with reference to the appended claims along with their full scope of equivalents.

What is claimed is:

1. An end effector arrangement of a minimally invasive surgical instrument, the end effector arrangement comprising:
   a first end effector mounting formation having a proximal end portion and a distal end portion which includes a first distal pivot location;
   a second end effector mounting formation having a proximal end portion and a distal end portion which includes a second distal pivot location, the distal end portions of the first and second end effector mounting formations being rotatably coupled together at the first and second distal pivot locations to rotate with respect to each other, each end effector mounting formation being arranged to carry an end effector element;
   a first pulley rotatable about a first center of rotation and having a first force transfer location spaced from the first center of rotation, the proximal end portion of the first end effector mounting formation being rotatably coupled with the first pulley at the first force transfer location to rotate with respect to one another; and
   a second pulley rotatable about a second center of rotation and having a second force transfer location spaced from the second center of rotation, the proximal end portion of the second end effector mounting formation being rotatably coupled with the second pulley at the second force transfer location to rotate with respect to one another.

2. The end effector arrangement of claim 1 wherein the first and second centers of rotation are aligned, and wherein the first and second pulleys are rotatably coupled together at the centers of rotation to rotate with respect to one another.

3. The end effector arrangement of claim 2 wherein the first and second pulleys are rotatably coupled together to rotate with respect to one another in a plane of movement, and wherein the first and second end effector mounting formations are rotatably coupled together to rotate with respect to one another in the plane of movement.

4. The end effector arrangement of claim 1 wherein the first and second end effector mounting formations are rotatably coupled together to move the end effector elements toward one another to contact at a contact position and away from one another generally in a plane of movement.

5. The end effector arrangement of claim 4 wherein the first and second force transfer locations are generally aligned with one another along a direction generally perpendicular to the plane of movement when the first and second end effector mounting formations are arranged to position the end effector elements in the contact position.

6. The end effector arrangement of claim 5 wherein the centers of rotation of the first and second pulleys are disposed between the generally aligned first and second force transfer locations and the rotatably coupled first and second distal pivot locations of the end effector mounting formations in the contact position.

7. The end effector arrangement of claim 5 wherein the centers of rotation of the first and second pulleys, the first and second force transfer locations, and the first and second distal pivot locations of the end effector mounting formations lie generally on a mid-plane which is perpendicular to the plane of movement when the first and second end effector mounting formations are arranged to position the end effector elements in the contact position.

8. The end effector arrangement of claim 1 wherein the first pulley has a first radius $R_1$ centered at the first center of rotation and the second pulley has a second radius $R_2$ centered at the second center of rotation, the first force transfer location being spaced from the first center of rotation of the first pulley by a first distance $d_1$ smaller than the first radius $R_1$, the second force transfer location being spaced from the second center of rotation of the second pulley by a second distance $d_2$ smaller than the second radius $R_2$.

9. The end effector arrangement of claim 8 wherein a ratio $R_1/d_1$ is at least about 2 and a ratio $R_2/d_2$ is at least about 2.

10. The end effector arrangement of claim 8 wherein the first radius $R_1$ is equal to the second radius $R_2$ and the first distance $d_1$ is equal to the second distance $d_2$, and wherein $R_1/d_1=R_2/d_2=R/d$.

11. The end effector arrangement of claim 10 wherein the first distal pivot location is spaced from the first force transfer location by a first distance $L_1$, and wherein the second distal pivot location is spaced from the second force transfer location by a second distance $L_2$.

12. The end effector arrangement of claim 11 wherein $L_1=L_2=L$.

13. The end effector arrangement of claim 12 wherein the end effector mounting formations are arranged to carry end effector elements having distal ends which are spaced from the rotatably coupled distal pivot locations by a distance l.

14. The end effector arrangement of claim 13 wherein $(R/d)(L/l)$ is at least about 1.

15. The end effector arrangement of claim 1 further comprising:
   a first channel formation extending at least partially circumferentially around the first pulley, the first channel formation defining opposed flange formations, one of the flange formations having a diameter less than the other flange formation; and
   a second channel formation extending at least partially circumferentially around the second pulley, the second channel formation defining opposed flange formations, one of the flange formations having a diameter less than the other flange formation.

16. An end effector arrangement of a minimally invasive surgical instrument, the end effector arrangement comprising:
   a first finger including a proximal end portion having a first finger transfer aperture, a distal end portion, and a first finger pivot hole disposed between the proximal end portion and the distal end portion;
   a second finger including a proximal end portion having a second finger transfer aperture, a distal end portion, and a second finger pivot hole disposed between the proximal end portion and the distal end portion, the first pivot hole and the second pivot hole being rotatably coupled for pivoting of the first and second fingers relative to one another;

a first pulley being rotatable about a first pulley pivot hole and having a first pulley transfer aperture spaced from the first pulley pivot hole, the first finger transfer aperture of the first finger being rotatably coupled with the first pulley transfer aperture for pivoting of the first finger and the first pulley relative to one another; and a second pulley being rotatable about a second pulley pivot hole and having a second pulley transfer aperture spaced from the second pulley pivot hole, the second finger transfer aperture of the second finger being rotatably coupled with the second pulley transfer aperture for pivoting of the second finger and the second pulley relative to one another.

17. The end effector arrangement of claim 16 wherein the first pulley pivot hole and the second pulley pivot hole are rotatably coupled for pivoting of the first and second pulleys relative to one another.

18. The end effector arrangement of claim 16 wherein the first and second finger pivot holes, the first and second pulley pivot holes, and the first and second pulley transfer apertures lie generally on a mid-plane, and wherein the first and second finger transfer apertures are disposed on opposite sides of the mid-plane during the full range of pivoting of the first and second fingers relative to one another.

19. The end effector arrangement of claim 18 wherein the first and second pulley pivot holes are disposed between the first and second finger pivot holes and the first and second pulley transfer apertures in the contact position.

20. The end effector arrangement of claim 16 wherein the first and second fingers are generally identical, and wherein the first and second pulleys are generally identical.

21. An end effector arrangement of a minimally invasive surgical instrument, the end effector arrangement comprising:

a first end effector mounting formation having a proximal end portion and a distal end portion which includes a first distal pivot location;

a second end effector mounting formation having a proximal end portion and a distal end portion which includes a second distal pivot location, the distal end portions of the first and second end effector mounting formations being rotatably coupled together at the first and second distal pivot locations to rotate with respect to each other, each end effector mounting formation being arranged to carry an end effector element;

a first force transfer member being rotatable about a first center of rotation by a first applied force normal to a first applied moment arm extending from the first center of rotation, the first force transfer member being coupled with a first transfer location in the proximal end portion of the first end effector mounting formation to transfer a first transfer force to the first transfer location in response to the first applied force, the first transfer force having a first normal force component normal to a first transfer moment arm extending from the first distal pivot location to the first transfer location, the first normal force component being equal to or larger than the first applied force; and a second force transfer member being rotatable about a second center of rotation by a second applied force normal to a second applied moment arm extending from the second center of rotation, the second force transfer member being coupled with a second transfer location in the proximal end portion of the second end effector mounting formation to transfer a second transfer force to the second transfer location in response to the second applied force, the second transfer force having a second normal force component normal to a second transfer moment arm extending from the second distal pivot location to the second transfer location, the second normal force component being equal to or larger than the second applied force.

22. The end effector arrangement of claim 21 wherein the first force transfer member comprises a first pulley, the first applied moment arm being generally equal to the radius of the first pulley, and wherein the second force transfer member comprises a second pulley, the second applied moment arm being generally equal to the radius of the second pulley.

23. The end effector arrangement of claim 21 wherein the first center of rotation of the first force transfer member and the second center of rotation of the second force transfer member are rotatably coupled together.

24. An end effector arrangement of a minimally invasive surgical instrument, the end effector arrangement comprising:

a first finger including a proximal end portion, a distal end portion, and a first finger pivot hole disposed between the proximal end portion and the distal end portion;

a second finger including a proximal end portion, a distal end portion, and a second finger pivot hole disposed between the proximal end portion and the distal end portion, the first finger pivot hole and the second finger pivot hole being rotatably coupled for pivoting of the first and second fingers relative to one another;

a first actuation member being rotatable about a first actuation member pivot hole;

first means coupled between the first finger and the first actuation member for transferring a first transfer force from the first actuation member to the first finger at a first transfer location in response to a first tangential force applied to the first actuation member, the first tangential force being normal to a radial direction extending radially from the first actuation member pivot hole, the first transfer force being normal to a first finger moment arm measured from the first finger pivot hole to the first transfer location, the first transfer force being equal to or greater than the first tangential force;

a second actuation member being rotatable about a second actuation member pivot hole; and second means coupled between the second finger and the second actuation member for transferring a second transfer force from the second actuation member to the second finger at a second transfer location in response to a second tangential force applied to the second actuation member, the second tangential force being normal to a radial direction extending radially from the second actuation member pivot hole, the second transfer force being normal to a second finger moment arm measured from the second finger pivot hole to the second transfer location, the second transfer force being equal to or greater than the second tangential force.

25. The end effector arrangement of claim 24 wherein first and second actuation member pivot holes are rotatably coupled for pivoting of the first and second actuation members relative to one another.

26. The end effector arrangement of claim 24 wherein the first transfer location is in the proximal end portion of the first finger and the second transfer location is in the proximal end portion of the second finger.

* * * * *